United States Patent [19]

Fukazawa et al.

[11] Patent Number: 5,106,579

[45] Date of Patent: * Apr. 21, 1992

[54] MEMBRANE TYPE ARTIFICIAL LUNG AND METHOD FOR MANUFACTURE THEREOF

[75] Inventors: Hiromichi Fukazawa, Fuji; Kazuhiko Hagiwara, Fujinomiya, both of Japan

[73] Assignee: Terumo Corporation, Tokyo, Japan

[ * ] Notice: The portion of the term of this patent subsequent to Mar. 20, 2007 has been disclaimed.

[21] Appl. No.: 589,020

[22] Filed: Sep. 27, 1990

Related U.S. Application Data

[63] Continuation of Ser. No. 462,869, Jan. 8, 1990, abandoned, which is a continuation of Ser. No. 906,099, Sep. 11, 1986, abandoned.

[30] Foreign Application Priority Data

Sep. 13, 1985 [JP] Japan ................... 60-201790
Sep. 13, 1985 [JP] Japan ................... 60-201791

[51] Int. Cl.$^5$ ............................................. A61M 1/14
[52] U.S. Cl. .................. 422/48; 210/321.62; 210/500.24; 210/500.27; 55/16; 55/158; 128/DIG. 3; 261/DIG. 28
[58] Field of Search ............. 422/48, 44; 128/DIG. 3; 261/DIG. 28; 55/16, 158; 210/321.62, 500.24, 500.27

[56] References Cited

U.S. PATENT DOCUMENTS

| | | | |
|---|---|---|---|
| 4,008,047 | 2/1977 | Petersen | 210/500.29 X |
| 4,210,529 | 7/1980 | Petersen | 210/321.3 X |
| 4,220,543 | 9/1980 | Yamashita | |
| 4,239,729 | 12/1980 | Hasegawa et al. | 422/48 |
| 4,374,802 | 2/1983 | Fukasawa | 210/321.3 X |
| 4,444,662 | 4/1984 | Conover | 422/48 X |
| 4,619,897 | 10/1986 | Hato et al. | 435/182 |

FOREIGN PATENT DOCUMENTS

| | | |
|---|---|---|
| 164025 | 12/1985 | European Pat. Off. |
| 2072047 | 9/1981 | United Kingdom |
| 2141752 | 1/1985 | United Kingdom |

OTHER PUBLICATIONS

Jinko Zoki, Artificial Organs, 12, Jpn. Jnl., pp. 358–361, (1983).
Jinko Zoki, Artificial Organs, 13, Jpn. Jnl., pp. 586–588, (1984).

Primary Examiner—Lynn M. Kummert
Attorney, Agent, or Firm—Cushman, Darby & Cushman

[57] ABSTRACT

A membrane type artificial lung uses a gas-exchange membrane having at least the surface thereof for exposure to blood or the minute pores therein coated or blocked with a vinyl type copolymer having as one of the components thereof a vinyl monomer possessing a perfluoroalkyl side chain. The gas-exchange membrane of the artificial lung is manufactured by a method which comprises bringing at least the surface of the gas-exchange membrane for exposure to blood into contact with a solution of the vinyl type copolymer and subsequently vaporizing the solvent in the solution.

19 Claims, 2 Drawing Sheets

MEMBRANE TYPE ARTIFICIAL LUNG AND METHOD FOR MANUFACTURE THEREOF

This is a continuation of application No. 07/462,869, filed Jan. 8, 1990, now abandoned which is a continuation of application Ser. No. 06/906,099 filed Sept. 11, 1986 now abandoned.

BACKGROUND OF THE INVENTION

1. Field of the Invention

This invention relates to a membrane type artificial lung and to a method for the manufacture thereof. More particularly, this invention relates to a membrane type artificial lung for removing carbon dioxide gas from blood and adding oxygen to blood during the course of extra-corporeal blood circulation. The artificial lung of the present invention exhibits biocompatibility, an insignificant loss of platelets, and excellent gas-exchange ability, and provide a method for the manufacture thereof.

2. Description of the Prior Art

Heretofore, as an auxiliary means for a cardiotomy, an artificial lung which is adapted to effect exchange of gases by exposing the blood in circulation to an oxygen-containing gas through the medium of a gas exchange membrane possessed of a satisfactory permeability to gas has been known. The gas-exchange membranes which are used in membrane type artificial lungs of the above described class are of two types, homogeneous membranes and porous membranes.

As homogeneous membranes, silicone membranes are currently used. However, since silicone membranes are used, the homogeneous membranes do not have sufficient strength for the membranes to be produced in a thickness below 100 μm. The membranes consequently have limited permeability to gas and exhibit particularly poor permeability to carbon dioxide gas. When some tens of thousands of hollow fiber membranes are bundled for the purpose of attaining a desired gas-exchange ability, the apparatus designed to operate with this bundle of membranes occupies a large volume, requires a large amount of priming, and proves very costly.

The porous membranes known in the art are made of various materials such as, for example, polyethylene, polypropylene, polytetrafluoroethylene, polysulfones, polyacrylonitrile, polyurethane, and polyamides. These gas-exchange membranes are required to possess large permeability coefficients with respect to $O_2$ and $CO_2$, refrain from inducing leakage of blood plasma during protracted circulation of blood, and avoid inflicting upon the blood damage due to physical contact as in the coagulation of blood, formation of microthrombosis, loss of platelets, degeneration of blood plasma proteins, and hemolysis. None of the gas-exchange membranes developed so far satisfies all these requirements. Particularly in terms of damage to blood or biocompatibility, even, silicone membranes which are rated as superior to all of the other membranes are still not satisfactory. In the extracorporeal circulation of blood such as in the use of an artificial lung, it has been customary to perform a chemotherapy for suppressing thrombosis by the addition of heparin simultaneously, for example. It has been found, however, that while the heparin can be expected to be effective in suppressing coagulation, it has virtually no effect upon the agglutination and aggregation of platelets.

The porous membranes literally possess numerous minute pores running throughout in the direction of wall thickness. Since the membranes are hydrophobic, they permit the addition of oxygen from the feed gas to blood and the removal of carbon dioxide gas from blood into the gas without the passage of blood plasma through the minute pores, i.e. leakage of blood plasma from the blood path side of the membrane to the gas path side thereof. Owing to their high permeability to steam, however, the porous membranes not only exhibit degradation of performance by dew, but also induce leakage of blood plasma during protracted service in circulation of blood. This adverse phenomenon is witnessed even in the case of those porous membranes which have successfully passed the water leakage test performed during the course of manufacture of an artificial lung.

With the goal towards eliminating the various drawbacks of the conventional porous membranes as described above, we have proposed an artificial lung using porous membranes having the minute pores thereof blocked with silicone oil (Japanese Patent Application SHO 58(1983)92,325) and a further improved artificial lung using porous membranes having the minute pores thereof blocked with silicone rubber (Japanese Patent Application SHO 59(1984)105,384). The artificial lung which uses porous membranes having the minute pores thereof blocked with silicone rubber no longer encounter the problem of blood plasma leakage which is observed in the artificial lungs using the conventional porous membranes. It nevertheless does not have the sufficient ability to remove carbon dioxide gas. As a result, it has experienced difficulties in removing the amount of carbon dioxide gas produced in the living body with such a low flow volume of blood as in the extracorporeal circulation such as, for example, the $ECCO_2R$ (extracorporeal $CO_2$ removal).

An object of this invention, therefore, is to provide a novel membrane type artificial lung and a method for the manufacture thereof.

Another object of this invention is to provide a membrane type artificial lung adapted to remove carbon dioxide gas from blood and add oxygen to the blood during the course of the extracorporeal circulation of blood. The artificial lung of the present invention has a greater ability to remove carbon dioxide gas and has no possibility of inducing leakage of blood plasma during a protracted use and a method for the manufacture thereof.

A further object of this invention is to provide a membrane type artificial lung which is most suitable for $ECCO_2R$ and a method for the manufacture thereof.

SUMMARY OF THE INVENTION

The objects of the present invention are accomplished by a membrane type artificial lung which is characterized in that the gas-exchange membranes incorporated therein have at least the surfaces thereof intended for exposure to blood coated with a vinyl type copolymer having as one of the components thereof a vinyl monomer possessing a perfluoroalkyl side chain.

This invention discloses a membrane type artificial lung, wherein the vinyl type copolymer is a methacrylate type copolymer having as one of the components thereof a methacrylate monomer possessing a perfluoroalkyl side chain. This invention also discloses a membrane type artificial lung, wherein the vinyl type copolymer is a block copolymer. This invention further discloses a membrane type artificial lung, wherein the weight ratio in the block copolymer of the polymer component formed of a vinyl monomer possessing a perfluoroalkyl side chain to the polymer component formed of the other monomer of the copolymer is in the range of 0.25 to 1.5. This invention discloses a membrane type artificial lung, wherein the perfluoroalkyl side chain is —$CH_2CH_2(CF_2)_7CF_3$. This invention also discloses a membrane type artificial lung, wherein the gas-exchange membranes are porous membranes. This invention further discloses a membrane type artificial lung, wherein the porous membranes are made of an olefin type resin. This invention discloses a membrane type artificial lung, wherein the porous membranes are made of polypropylene. This invention also discloses a membrane type artificial lung, wherein the gas-exchange membranes are homogeneous membranes. This invention further discloses a membrane type artificial lung, wherein the gas-exchange membranes are hollow fiber membranes. This invention also discloses a membrane type artificial lung, wherein the vinyl type copolymer having as one of the components thereof a vinyl monomer possessing a perfluoroalkyl side chain, is coated in a thickness in the range of 0.001 to 10 μm.

The objects described above are accomplished by a membrane type artificial lung using as gas-exchange membranes thereof porous membranes having a wall thickness in the range of 5 to 80 μm, a porosity in the range of 20 to 80%, and a pore diameter in the range of 0.01 to 5 μm, which artificial lung is characterized by having the minute pores thereof blocked with a vinyl type copolymer having as one of the components thereof a vinyl monomer possessing a perfluoroalkyl side chain.

This invention discloses a membrane type artificial lung, wherein the vinyl type copolymer is a methacrylate type polymer having as one of the components thereof a methacrylate monomer possessing a perfluoroalkyl side chain. This invention also discloses a membrane type artificial lung, wherein the vinyl type copolymer is a block copolymer. This invention further discloses a membrane type artificial lung, wherein the weight ratio in the vinyl type block copolymer of the polymer component formed of a vinyl monomer a possessing a perfluoroalkyl side chain to the polymer component formed of the other monomer of the copolymer is in the range of 0.25 to 1.5. This invention discloses a membrane type artificial lung, wherein the perfluoroalkyl side chain is —$CH_2CH_2(CF_2)_7CF_3$. This invention discloses a membrane type artificial lung, wherein the gas-exchange membranes are made of an olefin type resin. This invention discloses a membrane type artificial lung, wherein the gas-exchange membranes are made of polypropylene. This invention also discloses a membrane type artificial lung, wherein the gas-exchange membranes are hollow fiber membranes. This invention further discloses a membrane type artificial lung, wherein the hollow fiber membranes have an inside diameter in the range of 100 to 1,000 μm.

The above objects are accomplished by a method for the manufacture of a membrane type artificial lung, which method comprises bringing at least the surfaces of gas-exchange membranes intended for exposure to blood into contact with a solution of a vinyl type copolymer having as one of the components thereof a vinyl monomer possessing a perfluoroalkyl side chain and subsequently vaporizing the solvent of the solution thereby forming a coating of the vinyl copolymer on the surfaces for exposure to blood.

The above objects are accomplished by a method for the manufacture of a membrane type artificial lung using as gas-exchange membranes thereof porous membranes having a wall thickness in the range of 5 to 80 μm, a porosity in the range of 20 to 80%, and a pore diameter in the range of 0.01 to 5 μm, which method comprises bringing the porous hydrophobic membranes into contact with a solution of vinyl type copolymer having as one components thereof a vinyl monomer possessing a perfluoroalkyl side chain thereby blocking the minute pores of the membranes with the copolymer.

This invention also discloses a method for the manufacture of a membrane type artificial lung which further comprises bringing the surfaces for exposure to blood into contact with a cleaning liquid for the copolymer and subsequently vaporizing the cleaning liquid.

DESCRIPTION OF PREFERRED EMBODIMENT

Now, the present invention will be described in detail below with reference to the accompanying drawings.

Figure 1:
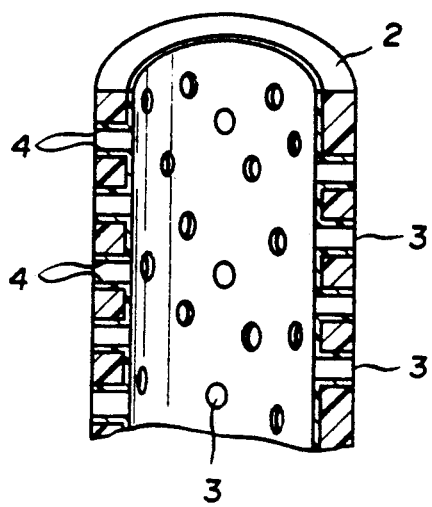
FIG. 1 is a model diagram illustrating one embodiment of the gas-exchange membrane to be used in the membrane type artificial lung of this invention,.
Figure 2:
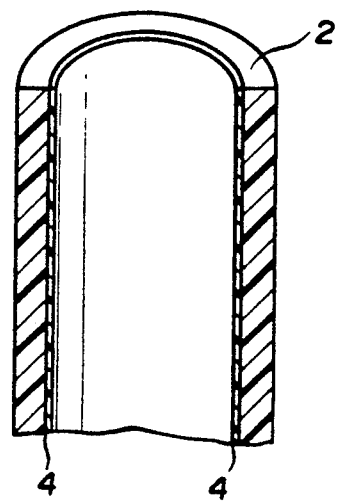
FIG. 2 is a model diagram illustrating another embodiment of the gas-exchange membrane.

FIG. 1 and FIG. 2 are magnified cross sections illustrating microstructures of membranes in typical membrane type artificial lungs embodying this invention.

The gas-exchange membrane 2 in the membrane type artificial lung 1 of the present invention is a porous membrane as illustrated in FIG. 1. It is otherwise a homogeneous membrane as illustrated in FIG. 2. When the gas-exchange membrane 2 is a porous membrane, the material used for the membrane is a macromolecular substance. Examples of the macromolecular substance include hydrophobic macromolecular substances such as polypropylene, polyethylene, polytetrafluoroethylene, polysulfones, polyacrylonitrile and cellulose acetate, and hydrophilic macromolecular substances, although hydrophobic substances are preferable. Among other materials enumerated above, olefin type resins are preferred and polypropylene is particularly preferred. A polypropylene membrane having minute pores formed therein by the stretching method or the solid-liquid layer separation method is preferable. This porous membrane has a wall thickness in the range of 5 to 80 μm, preferably 10 to 60 μm, a porosity in the range of 20 to 80%, preferably 30 to 60%, and a pore diameter in the range of 0.01 to 5.0 μm, preferably 0.01 to 1.0 μm. The gas-exchange membrane 2 of the present embodiment is a hollow fiber membrane having an inside diameter in the range of 100 to 1,000 μm, preferably 100 to 300 μm. When the gas-exchange membrane is a homogeneous membrane the material for the membrane is a silicone rubber, preferably a silicone rubber containing no silica. This homogeneous membrane has a wall thickness in the range of 50 to 300 μm, preferably 80 to 150 μm. The gas-exchange membrane 2 in this embodiment is a hollow fiber membrane having an inside diameter in the range of 100 to 1,000 μm, preferably 100 to 300 μm.

Further, the gas-exchange membrane 2 has at least the surface thereof for exposure to blood coated with a layer of a vinyl type copolymer having as one of the components thereof a vinyl monomer possessing a perfluoroalkyl side chain.

The vinyl type copolymer having as one component thereof a vinyl monomer possessing a perfluoroalkyl side chain is a copolymer of a desired vinyl type polymer with a vinyl monomer possessing a perfluoroalkyl side chain. Preferably, this copolymer is the so-called A-B type block copolymer which has a block of a homopolymer of a vinyl monomer possessing a perfluoroalkyl side chain linked to a mother block of a desired vinyl type polymer (which may be a homopolymer, a block copolymer, or a random copolymer). Typical examples of the vinyl monomer possessing a perfluoroalkyl side chain include perfluoroacrylates and perfluoromethacrylates which possess such perfluoroalkyl groups as $-CH_2(CF_2)_2H$, $-CH_2(CF_2)_4H$, $-CH_2CF_3$, and $-CH_2Ch_2(CF_2)_7CF_3$, preferably $-CH_2CH_2(CF_2)_7CF_3$, as side chains thereof. Typical examples of the vinyl monomer which forms the mother block are alkyl methacrylates such as methyl methacrylate, ethyl methacrylate, butyl methacrylate, and 2-ethylhexyl methacrylate, and alkyl acrylates such as methyl acrylate, ethyl acrylate, and butyl acrylate. In the vinyl type block copolymer having as one component thereof a vinyl monomer possessing a perfluoroalkyl side chain, the weight ratio of the polymer component formed of a vinyl monomer possessing a perfluoroalkyl side chain to the other vinyl monomer of the copolymer is in the range of 0.25 to 1.5, preferably 0.25 to 1.2. If this weight ratio is not more than 0.25, there is the possibility that the microstructural phase separation necessary for inhibiting agglutination of platelets will fail to manifest. If the weight ratio exceeds 1.5, there is the possibility that the solution of the copolymer with a solvent will become difficult and the fabricability of the copolymer will be degraded. This block copolymer is obtained by preparing a vinyl type polymer intended to constitute a mother block possessing a peroxy bond in the main chain thereof and polymerizing a perfluoroacrylate by dispersion polymerization using the vinyl polymer as a polymerization initiator.

The vinyl type block copolymer having as one component thereof a vinyl monomer possessing a perfluoroalkyl side chain is soluble in organic solvents embracing ketones such as acetone, methyl ethyl ketone, methyl isobutyl ketone, and cyclohexanone, alcohols such as methanol, ethanol, n-butanol, and sec-butanol, esters such as ethyl acetate and butyl acetate, ethers such as dimethylformamide, tetrahydrofuran, diethyl ether, methyl cellosolve, and ethyl cellosolve and chloroform.

The formation of a coating 4 of a vinyl type copolymer having as one of the components thereof a vinyl monomer possessing a perfluoroalkyl side chain on at least the surface of the gas-exchange membrane 2 for exposure to blood can be carried out easily as follows. To be specific, it is effected by bringing the surface of the gas-exchange membrane 2 for exposure to blood into contact, as by immersion, with a solution having the vinyl type copolymer dissolved therein in a concentration of 1 to 10% by weight, preferably 3 to 5% by weight and subsequently vaporizing the solvent of the solution. As the solvent to be used for this solution, though any of the solvents enumerated above can be adopted, it is preferable to adopt one member or a mixture of two or more members of the group aforementioned of ketones or a mixture of a ketone with an alcohol. Since it is necessary to control the vaporization of the solvent for the formation of a coating, it is proper to use a mixed solvent such as, for example, a 4/6 (volumetric ratio) mixture of methyl ethyl ketone/methyl isobutyl or a (4/6)10 volumetric ratio) mixture of methylethyl ketone/methyl isobutyl ketone)/ethanol. Although this coating of the gas-exchange membrane 2 with the vinyl type copolymer can be carried out before the membrane type artificial lung is assembled, it is carried out preferably after the assembly of the modules because the surface of the membrane type artificial lung for exposure to blood other than the gas-exchange membrane can be coated simultaneously with that of the gas-exchange membrane. The coating 4 of the vinyl type copolymer has thickness in the range of 0.01 to 10 μm, preferably 0.1 to 5 μm. If this thickness exceeds 10 μm, there is the possibility that the ability of the gas-exchange membrane to exchange gases will be lowered and there is also the possibility that when the gas-exchange membrane is a hollow fiber membrane, the blood passed in the hollow fiber will cause constriction of the blood path.

When the gas-exchange membrane is coated with the vinyl type copolymer having as one of the components thereof a vinyl monomer possessing a perfluoroalkyl side chain as described above, the otherwise possible damage done as to the platelet component of blood due to contact with the membrane will be suppressed to a great extent. Moreover, since the vinyl type copolymer a highly satisfactory permeability to gas, the coating does not have the possibility of substantially degrading the membrane type artificial lung's ability to add oxygen to blood and remove $CO_2$ from blood.

Figure 3:
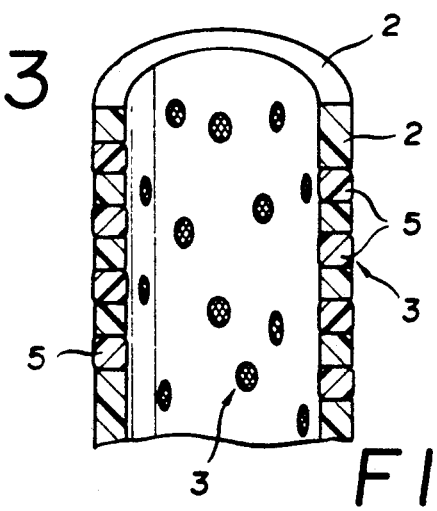
FIG. 3 is a model diagram illustrating yet another embodiment of the gas-exchange membrane.

FIG. 3 is a magnified cross section illustrating the microstructure of a gas-exchange membrane for use in a typical membrane type artificial lung embodying the present invention.

Figure 4:
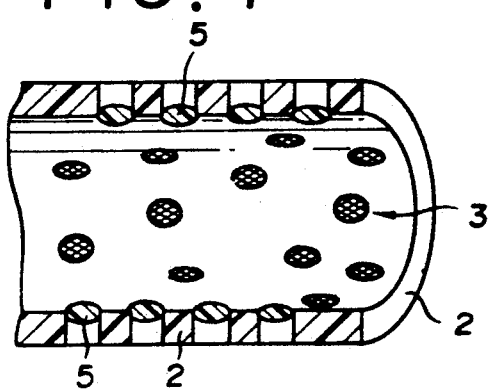
FIG. 4 is a model diagram illustrating a further embodiment of the gas-exchange membrane.
Figure 5:
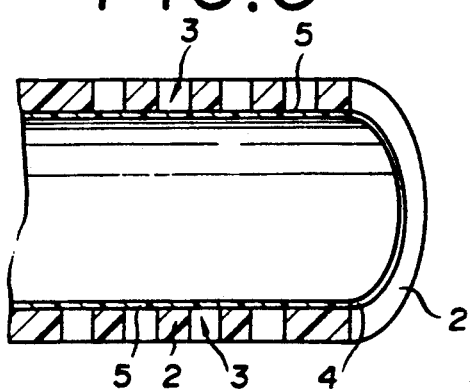
FIG. 5 is a model diagram illustrating still another embodiment of the gas-exchange membrane.

As illustrated in FIG. 3, the gas-exchange membrane 2 of the membrane type artificial lung is a hydrophobic porous membrane which has a wall thickness in the range of 5 to 80 μm, preferably 10 to 60 μm, a porosity in the range of 20 to 80%, preferably 30 to 60%, and a pore diameter approximately in the range of 0.01 to 5 μm, preferably 0.01 to 1.0 μm. In the present embodiment, the gas-exchange membrane is a hollow fiber membrane having an inside diameter in the range of 100 to 1,000 μm, preferably 100 to 300 μm. The minute pores 3 in the gas-exchange membrane 2 are blocked with a vinyl type block copolymer 5 having as one of the components thereof a vinyl monomer possessing a perfluoroalkyl side chain. For the purpose of this blocking, it suffices to close the greater part, if not all, of the minute pores. Preferably, all the minute pores are to be blocked. The minute pores 3 in the case of the present embodiment are blocked in a manner having the interiors thereof filled up with the vinyl type copolymer 5. Alternatively, they may be blocked in a manner having the copolymer 5 deposited only on the surface parts of the minute pores on the inner surface side (or the outer surface side) of the gas-exchange membrane 2 as illustrated in FIG. 4 or in a manner having the copolymer 5 deposited in the form of a continuous film on the entire inner surface (or the outer surface) of the gas-exchange membrane 2 as illustrated in FIG. 5. Particularly, since the copolymer to be described in detail below not only excels in permeability to gas but also possesses extremely high biocompatibility, it is desirable that the inner surface intended for exposure to blood should be covered with a coating of the copolymer.

The material for the gas-exchange membrane 2 is a macromolecular substance. Examples of the material include hydrophobic macromolecular substances such as polypropylene, polyethylene, polytetrafluoroethylene, polysulfones, polyacrylonitrile, and cellulose acetate, and hydrophilic macromolecular substances, although a hydrophobic substance is preferable. Among other materials cited above, olefin type resins are preferable and polypropylene is particularly preferable. A polypropylene membrane having minute pores formed therein by the stretching technique or the solid-liquid layer separation technique is desirable.

The expression "vinyl type block copolymer having as one of the components thereof a vinyl monomer possessing a perfluoroalkyl side chain" has the same meaning as defined above. This block copolymer is used in the form of a solution in an organic solvent as described above.

The blocking of the minute pores 3 of the gas-exchange membrane 2 with the vinyl type copolymer 5 having as one of the components thereof a vinyl monomer possessing a perfluoroalkyl side chain can be carried out easily as follows. To be specific, it is accomplished by bringing the gas-exchange membrane 2 in the form of a hollow fiber membrane into thorough contact, as by inflow or immersion, with a solution containing the vinyl type copolymer in a concentration in the range of 1 to 20% by weight, preferably 3 to 10% by weight, optionally removing the part of the solution adhering to the part other than the minute pores 3 with a cleaning liquid (bad-solvent) incapable of dissolving the vinyl type copolymer such as hexanes, heptanes, octanes, petroleum ether, etc., and subsequently vaporizing the liquid. This cleaning liquid is desired to be intimately mixable with the solvent in the solution of the copolymer. For the solution of the vinyl type copolymer, any of the aforementioned solvents can be used. Preferably, one member or a mixture of two or more members selected from the group of ketones or a mixture of a ketone with an alcohol is used. It is nevertheless necessary to control vaporization of the solvent. It is, therefore, proper to use a 4/6 (volumetric ratio) mixed solvent of methyl ethyl, ketone/methyl isobutyl ketone or a (4/6)/10 (volumetric ratio) (methylethyl ketone/methyl isobutyl ketone)/ethanol, for example. Although the blocking of the minute pores 3 of the gas exchange membrane 2 with the vinyl type copolymer may be carried out before the assembly of the membrane type artificial lung, it is performed preferably after the assembly of modules.

Figure 6:
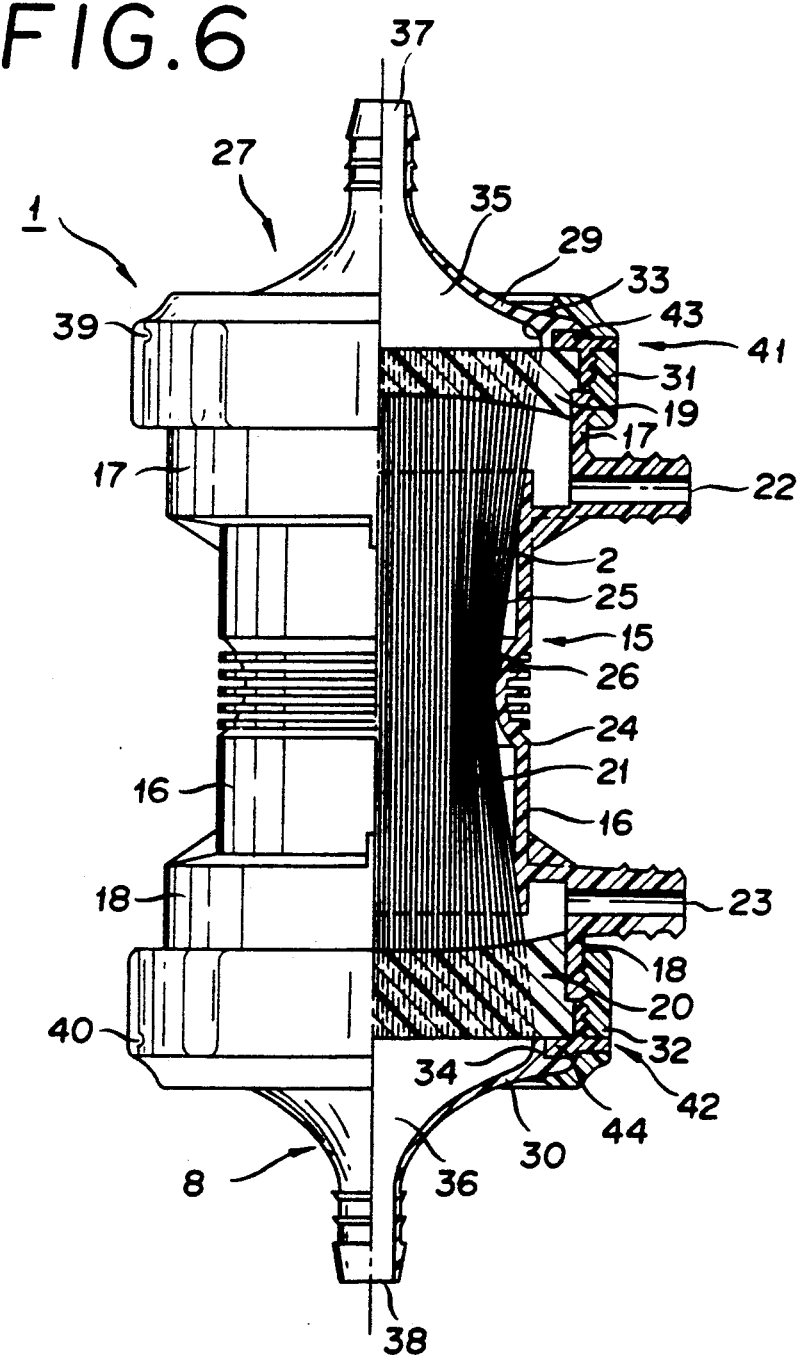
FIG. 6 is a partial cross section of a hollow fiber membrane type artificial lung as one embodiment of the membrane type artificial lung of this invention.

FIG. 6 illustrates the state in which a hollow fiber membrane type artificial lung as one embodiment of this invention is assembled. The hollow fiber membrane type artificial lung, is provided with a housing 15. This housing 15 comprises a cylindrical housing body 16 and annular externally threaded fitting covers 17, 18 disposed one each at the opposite ends of the annular housing body 16. Inside the housing 15, a multiplicity of, specifically 10,000 to 60,000 porous or homogeneous hollow fiber gas exchange membranes 2 having at least the surfaces thereof intended for exposure to blood coated with a vinyl type copolymer having as one of the components thereof a vinyl monomer possessing a perfluoroalkyl side chain described above or hollow fiber gas-exchange membranes 2 having the minute pores thereof blocked with a vinyl type copolymer having as one of the components thereof a vinyl monomer possessing a perfluoroalkyl side chain as described above are parallelly disposed along the direction of length of the housing 15 as mutually separated and spread throughout the entire cross-sectional area of the housing 15. The opposite ends of the gas-exchange membranes 2 are water-tightly supported in position respectively with bulkheads 19, 20 inside the fixing covers 17, 18 in such a manner that their openings will remain intact. The bulkheads 19,20 form an oxygen chamber 21, a chamber for transfer of a first substance, jointly with the outer surfaces of the gas-exchange membranes 2 and the inner surface of the housing 15, block the oxygen chamber 21, and separate the oxygen chamber 21 from a space for passage of block (not shown), a space for flow of a second substance, which is formed inside the gas-exchange membranes 2.

The fixing cover 17 is provided with an inlet 22 for feeding oxygen as the fluid for transfer of the first substance. The other fixing cover 18 is provided with an outlet 23 for discharging oxygen.

Preferably on the inner surface of the cylindrical housing body 16 of the housing 15, a constricting part 24 for compress the bundle of gas-exchange membranes is annularly raised at the central part in the axial direction. Specifically, the constricting part 24 is integrally formed with the cylindrical housing body on the inner surface of the cylindrical housing body so as to compress the periphery of the hollow fiber bundle 25 comprising the multiplicity of gas-exchange membranes 2 inserted inside the cylindrical housing body 16. As the result, the hollow fiber bundle 25 is compressed radially to form a compressed part 26 at the center in the axial direction as illustrated in FIG. 6. The packing ratio of gas-exchange membranes 2 varies at different parts along the axial direction and is highest at the central part. For the reason to be described afterward, preferred packing ratios at different parts are shown below. The packing ratio at the central compressed part 26 is approximately in the range of 60 to 80%, that inside the cylindrical housing body 16 is approximately in the range of 30 to 60%, and that at the opposite ends of the hollow fiber bundle 25, namely on the outer sides of the bulkheads 19, 20 is approximately in the range of 20 to 20%.

Now, the bulkheads 19, 20 will be described below with respect to their formation. As pointed out above, the bulkheads 19, 20 fulfill the important function of separating the interiors of the gas-exchange membranes 2 from the exteriors thereof. Generally, the bulkheads 19, 20 are produced by a macromolecular potting material of high polarity such as, for example, polyurethane, silicone, or epoxy resin by the centrifugal casting method into the cavities defined by the inner walls of the opposite ends of the housing 15 curing the cast material. To be more specific, a multiplicity of hollow fiber membranes 2 of a length greater than the length of the housing 15 are prepared, with the openings at the opposite ends thereof provisionally stoppered with highly viscous resin, and are parallelly disposed inside the cylindrical housing body 16 of the housing 15. Then, mold covers of a diameter greater than the diameter of the fixing covers 17, 18 are placed to cover the opposite ends of the gas-exchange membranes 2 completely and, with the housing 15 kept rotated around the axis thereof, the macromolecular potting material is injected inwardly from the opposite ends. When the injection is completed and the resin is cured, the mold covers are removed and the outer end surfaces of the cured resin are cut away with a sharp blade to expose the opposite opening ends of the gas-exchange membranes 2. In this manner, the bulkheads 19, 20 are completed.

The outer surfaces of the bulkheads 19, 20 are covered respectively by flow path forming members 27, 28 each provided with an annular projection. The flow path forming members 27, 28 comprises respectively liquid distributing members 29, 30 and threaded rings 31, 32. The end surfaces of raised strips 33, 34 formed as annular protuberances near the peripheries of the liquid distributing members 29, 30 are held fast respectively against the bulkheads 19, 20 and fixed in position by having helically fitting the threaded rings 31, 32 respectively into the covers 17, 18, with the result that an inflow chamber 35 and an outflow chamber 36 are formed for handling blood as the fluid for transfer of the second substance. In the flow path forming members 27, 28, an inlet 37 and an outlet 38 for the blood as the fluid for transfer of the second substance are formed.

The gaps formed around the peripheries of the bulkheads 19, 20 by the bulkheads 19, 20 and the flow path forming members 27, 28 are sealed tightly with the bulkheads 19, 20 by being filled with packing agents 43, 44 introduced through at least two holes 41, 42 communicating with the gaps. Otherwise, the gaps may be sealed with O-rings (not shown).

In the hollow fiber membrane type artificial lung described above, the fluid for transfer of the first substance is an oxygen-containing gas such as air or blood and the fluid for transfer of the second substance is blood or an oxygen-containing gas. When the fluid for transfer of the first substance is a gas, the fluid for transfer of the second substance is blood. When the fluid for transfer of the first membrane is blood, then the fluid for transfer of the second substance is a gas.

The present invention has been described with respect to the hollow fiber membrane type artificial lung. In the case of a flat membrane type artificial lung using a plurality of superposed membranes, one coiled membrane, or one membrane folded in a zigzag pattern, when the membranes having at least the surfaces thereof intended for exposure to blood coated with a vinyl type copolymer having as one of the components thereof a vinyl monomer possessing a perfluoroalkyl side chain or the minute pores in the gas-exchange membrane blocked with the copolymer is used, there is obtained a membrane type artificial lung which exhibits biocompatibility, or insignificant loss of platelets, excels in gas-exchange ability, particularly in the removal of $CO_2$, and avoids inducing any leakage of blood plasma during the course of protracted use.

Now, the present invention will be described more specifically below with reference to working examples.

EXAMPLE 1 AND CONTROL 1

A hollow fiber membrane type artificial lung having a membrane area of 1.6 $m^2$ and constructed as illustrated in FIG. 6 was produced using hollow fiber membranes of silicone rubber having an inside diameter of 200 μm and a wall thickness of 100 μm.

A 3 wt% solution was obtained separately by dissolving a (methyl methacrylate/butyl methacrylate)-perfluoropropyl acrylate block copolymer [weight ratio (25 : 25) : 50] in a 4/6 mixed solvent of methyl ethyl ketone/methyl isobutyl ketone. This (methyl methacrylate/butyl methacrylate)-perfluoropropyl acrylate copolymer solution was left in contact for 1 minute with the bloodflow surface of the aforementioned hollow fiber membrane type artificial lung. Then, the artificial lung was emptied of the solution and swept with air to remove the solvent and form a coating. To test the membrane type artificial lung thus formed with the coating (Example 1) and the membrane type artificial lung which had not undergone the coating treatment (Control 1) for gas-exchange ability, a venous blood adapted to have a partial pressure of oxygen of 35 mmHg and a partial pressure of carbon dioxide gas of 45 mmHg was prepared using fresh heparin-added bovine blood and caused to pass through the blood path of the artificial lung. The bovine blood used for this test had a hemoglobin content of 12 g/dl and a temperature of 37° C.

The relation between the flow volume of blood on one part and the ability to add oxygen gas and the ability to remove carbon dioxide gas on the other part where the ratio of the flow volume of oxygen to that of blood is as shown in Table 1. It is noted from Table 1 that substantially no difference of gas-exchange ability is recognized between the membrane type artificial lung of Example 1 and that of Control 1.

When these membrane type artificial lungs were subjected to 6 hours vein-artery extracorporeal circulation each using a dog, the loss of platelets was found to be 5% in the membrane type artificial lung of Example 1 and 15% in that of Control 1.

EXAMPLE 2 AND CONTROL 2

A hollow fiber membrane type artificial lung having a membrane area of 1.6 $m^2$ and constructed as illustrated in FIG. 6 was produced using porous hollow fiber membranes of polypropylene having an inside diameter of 200 μm, a wall thickness of 25 μm, a porosity of 45%, and an average pore diameter of 700 Å.

Separately, a 30 wt% solution was prepared by dissolving a (methyl methacrylate/butyl methacrylate)-perfluoropropyl acrylate block copolymer [weight ratio (25:25) : 50] in a 4/6 mixed solvent of methyl ethyl ketone/methyl isobutyl ketone and then was diluted with ethanol to 3% by weight. With this diluted solution, a coating was formed on the blood flow surface of the hollow fiber membrane type artificial lung by following the procedure of Example 1. The membrane type artificial lung formed with the coating (Example 2) and the membrane type artificial lung which had not undergone the coating treatment (Control 2) were tested for gas-exchange ability by following the procedure of Example 1 and Control 1. The results were as shown in Table 1. It is noted from Table 1 that substantially no difference of gas-exchange ability was recognized between the membrane type artificial lung of Example 2 and that of Control 2.

When these membrane type artificial lungs were subjected to 30 hours vein-artery extracorporeal circulation each using a mongrel dog, the loss of platelets was found to be 10% in the membrane type artificial lung of Example 2 and 25% in that of Control 2.

TABLE 1

| | Volume of gas transfered (ml/min) | | | | |
|---|---|---|---|---|---|
| | Flow volume of blood (liter/min.) | | | | |
| | 0 | 0.5 | 1.0 | 1.5 | 2.0 |
| Example 1 | | | | | |
| $CO_2$ | 0 | 28 | 45 | 62 | 75 |
| $O_2$ | 0 | 30 | 53 | 70 | 77 |
| Control 1 | | | | | |
| $CO_2$ | 0 | 29 | 47 | 61 | 73 |
| $O_2$ | 0 | 30 | 54 | 71 | 76 |
| Example 2 | | | | | |
| $CO_2$ | 0 | 32 | 61 | 85 | 107 |
| $O_2$ | 0 | 33 | 56 | 75 | 82 |
| Control 2 | | | | | |
| $CO_2$ | 0 | 33 | 64 | 89 | 114 |
| $O_2$ | 0 | 32 | 58 | 76 | 84 |

EXAMPLE 3 AND CONTROL 3

A hollow fiber membrane type artificial lung having a membrane area of 1.6 m² and constructed as illustrated in FIG. 6 was produced using hollow fiber membranes of polypropylene having an inside diameter of 200 μm, a wall thickness of 25 μm, a porosity of 45%, and an average pore diameter of 700 Å.

Separately, a 30 vol% solution was prepared by dissolving a (methyl methacrylate/butyl methacrylate)-perfluoropropyl acrylate block copolymer [weight ratio (25 : 25) : 50 ] in a 4/6 mixed solvent of methyl ethyl ketone/methyl isobutyl ketone and then diluted with ethanol to 6 wt%. The hollow fiber membranes of the hollow fiber membrane type artificial lung were kept filled for 3 minutes with the (methyl methacrylate/butyl methacrylate)-perfluoropropyl acrylate copolymer solution, then emptied of the solution, divested of the residual solvent, and dried, to give rise to a coating serving to block the minute pores in the membrane. To test the membrane type artificial lung formed with the coating (Example 3) and the membrane type artificial lung which has not undergone the treatment with the (methyl methacrylate/butyl methacrylate)-perfluoropropyl acrylate copolymer (Control 3) for gas-exchange ability, a venous blood adapted to have a partial pressure of oxygen gas of 35 mm Hg was produced using fresh heparin-added bovine blood and passed though the blood path of the artificial lung. The bovine blood used in the test had a hemoglobin content of 12 g/dl and a temperature of 37° C.

The relation between the flow volume of blood on one part and the ability to add oxygen gas and the ability to remove carbon dioxide gas on the other hand existing when the ratio of the flow volume of oxygen to that of blood is 1 is as shown in Table 2. It is noted from Table 2 that substantially no difference of gas-exchange ability is recognized between the membrane type artificial lung of Example 3 and that of Control 3.

When the membrane type artificial lungs were subjected to 30 hour vein-artery extracorporeal circulation each using a mongrel dog, absolutely no leakage of blood plasma occurred in the membrane type artificial lung of Example 3, whereas leakage of blood plasma started after 8 hours circulation in the membrane type artificial lung of Control 3.

EXAMPLE 4 AND CONTROL 4

A hollow fiber membrane type artificial lung having a membrane area of 1.6 m² and constructed as illustrated in FIG. 6 was produced using the same hollow fiber membrane of polypropylene as used in Example 3.

The hollow fiber membranes of the hollow fiber membrane type artificial lung were kept filled for 3 minutes with the same (methyl ethyl ketone/methyl isobutyl ketone)/ethanol solution of a (methyl methacrylate/butyl methacrylate)-perfluoropropyl acrylate block copolymer as used in Example 3, emptied of the solution, and n-hexane was passed through the membranes then they were dried. Consequently, the minute pores in the hollow fiber membranes were blocked with the (methyl methacrylate/butyl methacrylate)-perfluoropropyl acrylate copolymer (Example 4).

Then, the hollow fiber membranes of the hollow fiber membrane type artificial lung were kept filled for 1 minute with a trifluorochloroethane 60 wt% silicone solution, emptied of the solution, then swept with a toluene/dipropylene glycol solution to wash out the residual silicone rubber solution adhering to the interiors of the hollow fiber membranes with silicone rubber (Control 4). When the two artificial lungs were tested for ability to exchange carbon dioxide gas by circulating blood at a flow rate of 1,500 ml/min and feeding oxygen gas at a flow volume of 15 liters/min, the exchange ability was found to be 250 ml/min in Example 4 and 160 ml/min in Control 4, indicating that the artificial lung of Example 4 filled with the (methyl methacrylate/butyl methacrylate)-perfluoropropyl acrylate copolymer was applicable to LFPPV-ECCO₂R, whereas p the artificial lung of Control 4 filled with the silicone rubber had too poor ability to exchange carbon dioxide gas to be applied effectively to LFPPV-ECCO₂R.

TABLE 2

| | Volume of gas transfered (ml/min) | | | | |
|---|---|---|---|---|---|
| | Flow volume of blood (liter/min.) | | | | |
| | 0 | 0.5 | 1.0 | 1.5 | 2.0 |
| Example 3 | | | | | |
| $CO_2$ | 0 | 32 | 58 | 82 | 101 |
| $O_2$ | 0 | 32 | 54 | 76 | 80 |
| Control 3 | | | | | |
| $CO_2$ | 0 | 33 | 64 | 89 | 114 |
| $O_2$ | 0 | 32 | 58 | 76 | 84 |

Since the present invention is directed to a membrane type artificial lung characterized by causing at least the surface of the gas-exchange membrane intended for exposure to blood to be coated with a vinyl type copolymer having as one of the components thereof a vinyl monomer possessing a perfluoroalkyl side chain, the membrane type artificial lung inflicts upon the blood being circulated only insignificant damage as in the form of coagulation of blood, formation of microthrombosis, loss of platelets, degeneration of blood plasma proteins, hemolysis, etc. and thus, exhibits high biocompatibility. Further, the membrane type artificial lung possesses sufficient gas-exchange ability because the coating of the vinyl monomer possessing a perfluoroalkyl side chain has extremely high permeability to gas and does not impair the gas-exchange ability inherent in the gas-exchange membrane. This invention, therefore, provides excellent membrane type artificial lung.

This invention, as described above, is directed to a membrane type artificial lung using gas-exchange membranes having a wall thickness in the range of 5 to 80 μm, a porosity in the range of 20 to 80%, and a pore diameter in the range of 0.01 to 5μm, which membrane type artificial lung is characterized by having the minute pores in the membranes blocked with a vinyl type copolymer having as one of the components thereof a vinyl monomer possessing perfluoroalkyl side chain. In spite of its extremely high ability to exchange gases, particularly to remove carbon dioxide gas, this membrane type artificial lung does not induce leakage of blood plasma during a protracted use. It is, therefore, capable of removing the amount of carbon dioxide gas produced in the living body with such a small extracorporeal circulation volume as $ECCO_2R$.

The membrane type artificial lung of this invention exhibits the gas-exchange ability to great advantage when the vinyl type copolymer is a methacrylate type copolymer having as one of the components thereof a methacrylate monomer possessing a perfluoroalkyl side chain, when the vinyl copolymer is a block copolymer, when the weight ratio in the vinyl type block copolymer of the polymer component formed of a vinyl monomer possessing a perfluoroalkyl side chain to the polymer component formed of the other monomer of the copolymer is in the range of 0.25 to 1.5, and when the perfluoroalkyl side chain is $-CH_2CH_2(CF_2)_7CF_3$. The membrane type artificial lung exhibits a particularly high biocompatibility when the vinyl type block copolymer of the foregoing description further coats the surface of the artificial lung destined to contact blood. The gas-exchange membranes acquire sufficient mechanical strength to warrant compaction of the artificial lung when they are made of an olefin type resin, preferably polypropylene. The membrane type artificial lung is enabled to exhibit outstanding performance when the gas-exchange membranes are hollow fiber membranes.

What is claimed is:

1. A gas-exchange membrane for an artificial lung, comprising a membrane having a surface coated with a vinyl type copolymer comprising a methacrylate type copolymer comprising a methacrylate monomer possessing a perfluoroalkyl side chain which is exposed to blood.

2. A gas-exchange membrane for an artificial lung according to claim 1, wherein said vinyl type copolymer is a block copolymer.

3. A gas-exchange membrane for an artificial lung according to claim 2, wherein the weight ratio of a polymer component formed of a vinyl monomer possessing a perfluoroalkyl side chain to a polymer component formed of another monomer of said block copolymer is in the range of 0.25 to 1.5.

4. A gas-exchange membrane for an artificial lung according to claim 1, wherein said perfluoroalkyl side chain is $-Ch_2CH_2(CF_2)_7CF_3$.

5. A gas-exchange membrane for an artificial lung according to claim 1, wherein said membrane is a porous membrane.

6. A gas-exchange membrane for an artificial lung according to claim 5, wherein said porous membrane is made of an olefin type resin.

7. A gas-exchange membrane for an artificial lung according to claim 6, wherein said membrane is made of polypropylene.

8. A gas-exchange membrane for an artificial lung according to claim 1, wherein said membrane is a homogeneous membrane.

9. A gas-exchange membrane for an artificial lung according to claim 8, wherein said homogeneous membrane is made of silicone rubber.

10. A gas-exchange membrane for an artificial lung according to claim 1, wherein said membrane is a hollow fiber membrane.

11. A gas-exchange membrane for an artificial lung according to claim 1, wherein said vinyl type copolymer comprises a vinyl monomer possessing a perfluoroalkyl side chain applied in a wall thickness in the range of 0.001 to 10 $\mu m$.

12. A gas-exchange membrane for an artificial lung comprising a porous membrane having a wall thickness in the range of 5 to 80 $\mu m$, a porosity in the range of 20 to 80%, and a pore diameter in the range of 0.01 to 5 $\mu m$, wherein said porous membrane comprises minute pores blocked with a vinyl type copolymer of a methacrylate type copolymer comprising a methacrylate monomer possessing a perfluoroalkyl side chain and said porous membrane is coated with said vinyl type copolymer on a side wall exposed to blood.

13. A gas-exchange membrane for an artificial lung according to claim 12, wherein said vinyl type copolymer is a block copolymer.

14. A gas-exchange membrane for an artificial lung according to claim 13, wherein the weight ratio of a polymer component formed of a vinyl monomer possessing a perfluoroalkyl side chain to a polymer component formed of another monomer of said vinyl type block copolymer is in the range of 0.25 to 1.5.

15. A gas-exchange membrane for an artificial lung according to claim 12, wherein said perfluoroalkyl side chain is $-CH_2CH_2(CF_2)_7CF_3$.

16. A gas-exchange membrane for an artificial lung according to claim 12, wherein said porous membrane is made of an olefin type resin.

17. A gas-exchange membrane for an artificial lung according to claim 16, wherein said membrane is made of polypropylene.

18. A gas-exchange membrane for an artificial lung according to claim 12, wherein said membrane is a hollow fiber membrane.

19. A gas-exchange membrane of an artificial lung according to claim 18, wherein said hollow fiber membrane has an inside diameter in the range of 100 to 1,000 $\mu m$.

* * * * *